(12) United States Patent
Thakkar

(10) Patent No.: US 12,318,163 B2
(45) Date of Patent: Jun. 3, 2025

(54) STRAIN WAVE GEARING WITH INPUT TO OUTPUT BRAKING

(71) Applicant: Verb Surgical Inc., Santa Clara, CA (US)

(72) Inventor: Bharat Thakkar, Campbell, CA (US)

(73) Assignee: Verb Surgical Inc., Santa Clara, CA (US)

( * ) Notice: Subject to any disclaimer, the term of this patent is extended or adjusted under 35 U.S.C. 154(b) by 201 days.

(21) Appl. No.: 18/316,665

(22) Filed: May 12, 2023

(65) Prior Publication Data

US 2023/0355336 A1 Nov. 9, 2023

Related U.S. Application Data

(63) Continuation of application No. 16/520,196, filed on Jul. 23, 2019, now Pat. No. 11,696,806.

(51) Int. Cl.

| | |
|---|---|
| *F16H 49/00* | (2006.01) |
| *A61B 34/00* | (2016.01) |
| *A61B 34/30* | (2016.01) |
| *A61B 50/15* | (2016.01) |
| *B25J 9/10* | (2006.01) |
| *B25J 19/00* | (2006.01) |
| *F16D 13/00* | (2006.01) |
| *F16D 27/00* | (2006.01) |

(52) U.S. Cl.
CPC .............. *A61B 34/70* (2016.02); *A61B 34/30* (2016.02); *A61B 50/15* (2016.02); *B25J 9/102* (2013.01); *B25J 9/1025* (2013.01); *B25J 19/0004* (2013.01); *F16D 13/00* (2013.01); *F16D 27/00* (2013.01); *F16H 49/001* (2013.01)

(58) Field of Classification Search
CPC .... B25J 9/1025; B25J 19/0004; F16H 49/001
See application file for complete search history.

(56) References Cited

U.S. PATENT DOCUMENTS

| | | |
|---|---|---|
| 9,636,184 B2 | 5/2017 | Lee et al. |
| 2007/0101820 A1 | 5/2007 | Bulatowicz |
| | (Continued) | |

FOREIGN PATENT DOCUMENTS

| | | |
|---|---|---|
| CN | 101703826 B | 10/2011 |
| EP | 3101314 A1 | 12/2016 |
| | (Continued) | |

OTHER PUBLICATIONS

Global Harmonic Drive Precision Strain Wave Reducer Gearboxes and RV and RD Reducers Market 2018-2024; Research and Markets; Dec. 2017, 4 Pages, <https://www.globenewswire.com/news-release/2017/12/20/1266821/O/en/Global-Harmonic-Drive-Precision-Strain-Wave-Reducer-Gearboxes-and-RV-and-RD-Reducers-Market-2018-2024.html>.

(Continued)

*Primary Examiner* — Randell J Krug
(74) *Attorney, Agent, or Firm* — Aikin & Gallant, LLP

(57) ABSTRACT

A braking assembly for a strain wave gearing of a surgical robotic manipulator, the braking assembly including a first braking member fixedly coupled to an input portion of a strain wave gearing of a surgical robotic manipulator; and a second braking member fixedly coupled to an output portion of the strain wave gearing, and wherein during a braking operation the first braking member contacts the second braking member to mechanically brake the input portion to the output portion.

20 Claims, 9 Drawing Sheets

(56) References Cited

U.S. PATENT DOCUMENTS

| | | |
|---|---|---|
| 2017/0222517 A1 | 8/2017 | Kobayashi |
| 2018/0177470 A1 | 6/2018 | Suga et al. |
| 2018/0215050 A1* | 8/2018 | Kassow ............... B25J 19/0004 |
| 2019/0099880 A1 | 4/2019 | Niu |

FOREIGN PATENT DOCUMENTS

| | | |
|---|---|---|
| JP | 6148359 B2 | 6/2017 |
| WO | 2007/082594 A2 | 7/2007 |
| WO | 2017/203231 A1 | 11/2017 |
| WO | 2019/039131 A1 | 2/2019 |

OTHER PUBLICATIONS

Harmonic Drive LLC X-Ray Machine C-Beam Drive, Application Handbook Medical Equipment, 1 Page, Retrieved on Oct. 2018, <https://www.harmonicdrive.net/_hd/content/.../XRayMachineCBeamDrive.pdf>.

International Preliminary Report on Patentability received for PCT Patent Application No. PCT/US19/043286, mailed on Feb. 3, 2022, 15 pages.

International Search Report and Written Opinion received for PCT Patent Application No. PCT/US19/043286, mailed on Jul. 7, 2020, 19 pages.

Invitation to Pay Additional Fees of the PCT Patent Office dated Apr. 15, 2020, for related PCT Patent Application No. PCT/US2019/043286.

Non-Final Office Action of the U.S. Patent Office dated Sep. 14, 2022 for related U.S. Appl. No. 16/520,196.

* cited by examiner

STRAIN WAVE GEARING WITH INPUT TO OUTPUT BRAKING

CROSS-REFERENCE TO RELATED APPLICATION

This application is a continuation of U.S. application Ser. No. 16/520,196, filed Jul. 23, 2019, entitled "STRAIN WAVE GEARING WITH INPUT TO OUTPUT BRAKING," which is hereby incorporated by reference in its entirety.

BACKGROUND

Field

Embodiments related to robotic systems, are disclosed. More particularly, embodiments related to a strain wave gearing with input to output braking for a surgical robotic manipulator, are disclosed.

Background

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted components and tools. For example, a surgical robotic system may include a number of surgical robotic manipulators, including surgical robotic arms, that are mounted to a surgical table and manipulated to perform surgical procedures. It is important, however, for the surgical robotic manipulators to be precisely manipulated and maintained in a desired orientation and/or configuration during a surgical robotic procedure.

SUMMARY

A surgical robotic system may include a surgical robotic manipulator, for example a surgical robotic arm, including a number of links which are connected to one another, and to a fixed structure such as a surgical table, by joints. It is imperative that the various joints connecting the links and the robotic arm to the surgical table be capable of fluid motion and lockable in a desired position, particularly during a surgical operation. For example, a joint that mounts the surgical robotic arm to a surgical table may need to pivot the arm from a storage position, to an operating position, in which the arm is locked during the surgical procedure.

A rotary or pivot joint may include strain wave gearing (e.g., a Harmonic Drive®) which is made up of a wave generator, a flex spline and a rigid ring or circular spline. The wave generator (and its associated components) may be considered the input element, while the flex spline (and its associated components) may be considered the output element. In conventional gearing systems, a holding and/or stopping mechanism (brake) may be connected to the housing and used to restrict the motion of an output shaft or an input shaft relative to the housing. For example, the braking mechanism may be attached to a fixed housing within which the gearing system is implemented, and then mechanically (physically) engage the input shaft or the output shaft to brake (secure) the input shaft or the output shaft relative to the housing. One disadvantage of such a braking mechanism, however, is that because the brake must essentially brake the entire gearing system to the housing, it must be relatively large.

The proposed invention, on the other hand, includes a braking mechanism or assembly that mechanically brakes the wave generator (input) to the flex cup or spline (output), and can therefore be much smaller than traditional braking mechanisms. Representatively, the braking assembly may include a first braking member and a second braking member. The first baking member may be attached to an input shaft, which is rigidly coupled to the wave generator. The second braking member may be attached to the output (free) shaft, which is rigidly coupled to the flex cup. When the brake is engaged, the first member engages with the second member, which in turn, mechanically couples the wave generator (input) to the flex cup (output) so that they can no longer move relative to one another. Therefore, when the brake is engaged and either a forward or a back driving torque is applied, any motion of the gearbox is blocked. Said another way, the flex cup and wave generator are rigidly coupled to one another when the brake is engaged and the motion is prohibited. Because the braking mechanism is within the strain wave gearing, as opposed to a brake coupled to the housing, the braking mechanism may have a smaller envelope size and the overall gearbox may be smaller due to the torque reduction through the gearbox. Advantages of the assembly disclosed herein include (1) a reduction in holding torque of the braking assembly due to the high gear reduction and friction of the strain wave gearing, (2) a compact design envelope because the brake is packaged inside an already existing output/input shaft thereby reducing the overall footprint, and (3) since stopping and/or holding of the input member to the output member is done directly on the axis of rotation, the number of components between the output and the brake is reduced.

In one aspect, a braking assembly for a strain wave gearing of a surgical robotic manipulator is provided, the braking assembly may include a first braking member fixedly coupled to an input portion of a strain wave gearing of a surgical robotic manipulator; and a second braking member fixedly coupled to an output portion of the strain wave gearing, and wherein during a braking operation the first braking member contacts the second braking member to mechanically brake the input portion to the output portion. The first braking member and the second braking member may be axially aligned, and during the braking operation a top side of the first braking member contacts a bottom side of the second braking member preventing rotation of the input portion relative to the output portion. In some aspects, the braking assembly includes a spring set brake or a permanent magnet brake. In some cases, the first braking member includes a disk that is movable in an axial direction relative to the second braking member, the second braking member includes an electromagnet, and the braking operation occurs in the absence of power. The input portion may include an input shaft fixedly coupled to a wave generator that is rotatably coupled to the output portion, the first braking member may include a disk coupled to the input shaft, the output portion may include a flex cup that is rotatably coupled to the input portion, the second braking member is coupled to the flex cup, and a fixed portion is positioned concentrically outward to the input portion and the output portion. In some aspects, the surgical robotic manipulator may include a surgical robotic arm having a number of links connected by a number of joints, and one of the joints comprises the strain wave gearing.

In another aspect, a strain wave gearing of a surgical robotic manipulator is provided and includes an input portion, and output portion, a fixed portion and a braking assembly. The input portion may include a wave generator fixedly coupled to an input shaft. The output portion may include a flex cup fixedly coupled to an output shaft and having a number of flex cup teeth formed along an exterior surface of the flex cup, and the input portion is positioned within the output portion and rotates to drive a relative movement between the input portion and the output portion. The fixed portion may include a circular spline with a number of circular spline teeth formed along an interior surface of the circular spline, wherein the output portion is positioned within the fixed portion and the circular spline teeth engage with the flex cup teeth to rotate the output portion relative to the fixed portion. The braking assembly may include a first braking member coupled to the input portion and a second braking member coupled to the output portion, and the braking assembly may be operable to prevent a relative movement between the input portion and the output portion during a braking operation. In some aspects, a movement of the first braking member or the second braking member in an axial direction transitions the braking assembly between an engaged position in which the first braking member contacts the second braking member and a disengaged positon in which there is a gap between the first braking member and the second braking member. In some aspects, the first braking member is operable to rotate with the input shaft, and movable in an axial direction. The first braking member may include a top component and a bottom component, wherein the top component or the bottom component is operable to move in the axial direction relative to the other. The second braking member may include an electromagnet coil and a permanent magnet fixedly coupled to the output portion. The input portion, the output portion, the fixed portion and the braking assembly may be aligned along a common axis. The surgical robotic manipulator may include a surgical robotic arm having a number of links connected by a number of joints, and one of the joints connecting the surgical robotic arm to a fixed structure comprises the strain wave gearing.

In another aspect, the surgical robotic system may include a surgical table, a surgical robotic manipulator and a strain wave gearing. The surgical robotic manipulator may be coupled to the surgical table, the surgical robotic manipulator comprising a plurality of links and a plurality of joints that are operable to move with respect to one another to move the surgical robotic manipulator. The strain wave gearing may be coupled to at least one of the plurality of joints, the strain wave gearing comprising a wave generator, a flex cup, a circular spline and a braking assembly operable to prevent a relative movement between the wave generator and the flex cup during a braking operation. In some aspects, the surgical robotic manipulator may include a surgical robotic arm, at least one joint of the plurality of joints is a pivot joint connecting the surgical robotic arm to a surgical table, and the strain wave gearing is coupled to the pivot joint. The braking assembly may include a first braking member attached to the wave generator and a second braking member fixedly attached to the flex cup, and wherein the first braking member and the second braking member directly engage with one another during the braking operation. In some aspects, during a non-braking operation, the first braking member and the second braking member are operable to rotate relative to one another around a common axis. The first braking member may include a metal disk and the second braking member comprises a permanent magnet. The braking assembly may include a spring set brake. In some aspects, the wave generator, the flex cup, the circular spline and the braking assembly are aligned along a common axis.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
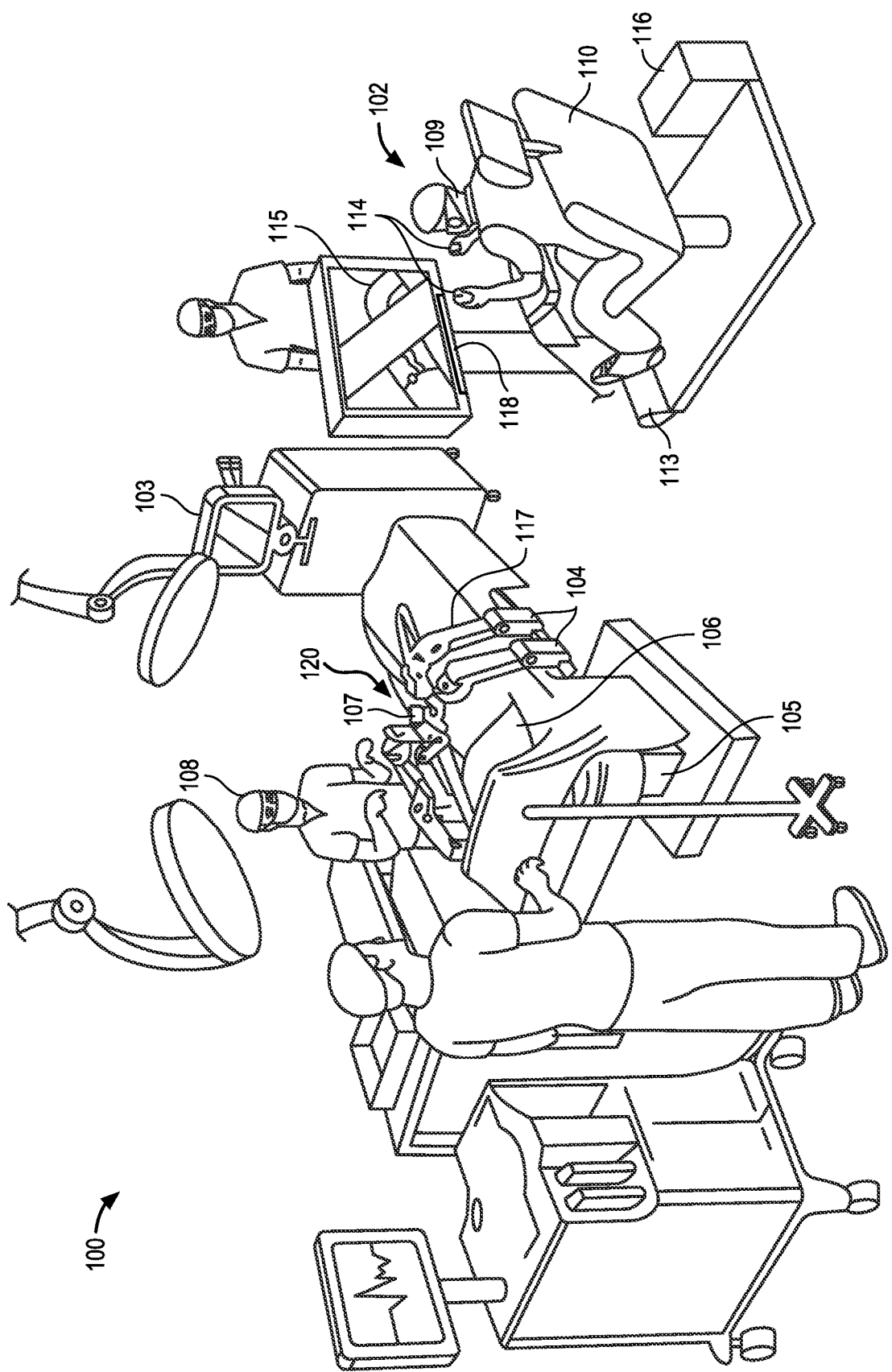
FIG. 1 is a pictorial view of an example surgical robotic system in an operating arena, in accordance with an embodiment.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Referring to FIG. 1, this is a pictorial view of an example surgical robotic system 100 in an operating arena. The surgical robotic system 100 includes a user console 102, a control tower 103, and one or more surgical robotic manipulators, for example, surgical robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, foot-operated controls 113, one or more handheld user input devices, UID 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104.)

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site.) Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the platform 105 and the user console 102 may be through a control tower 103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
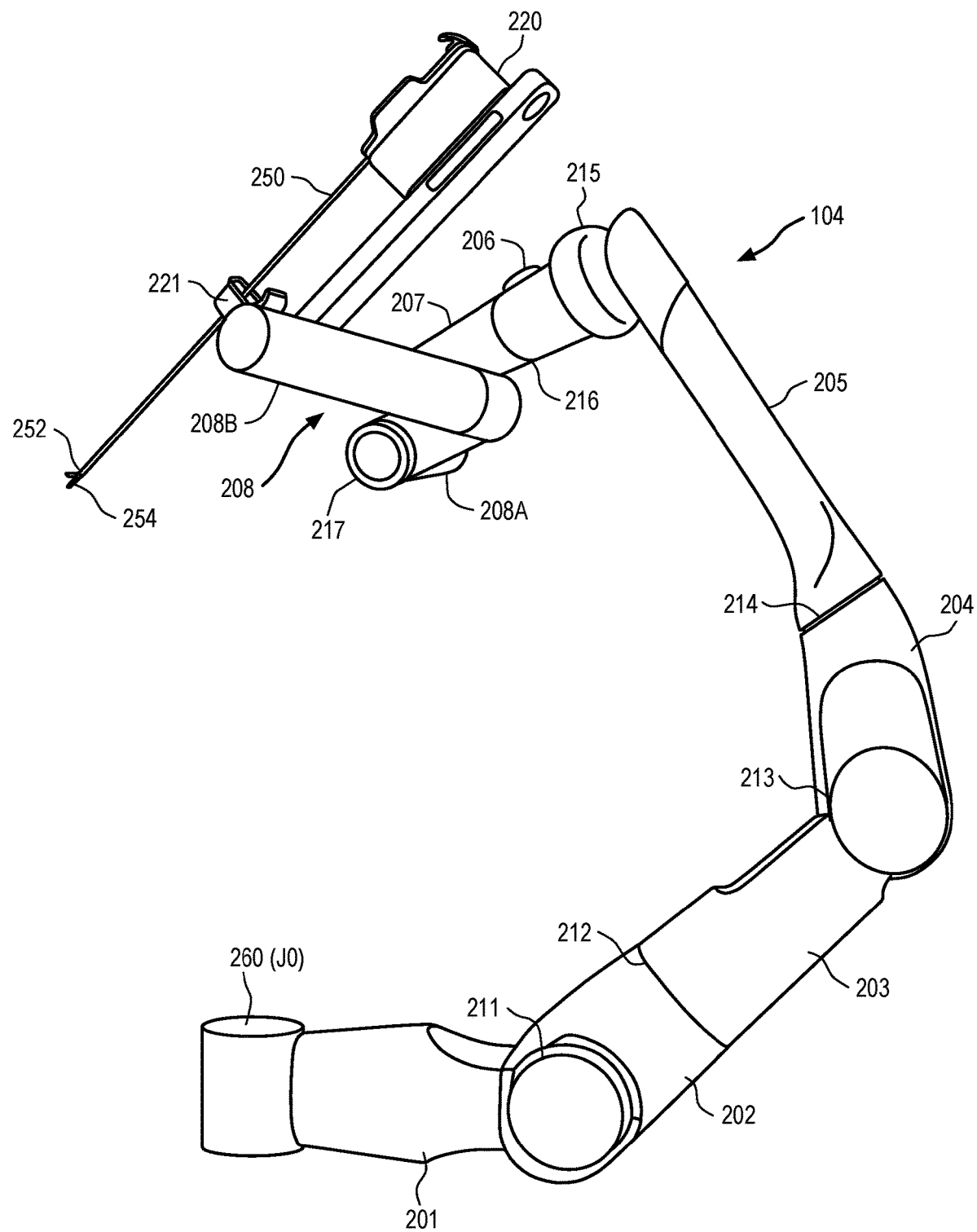
FIG. 2 is a pictorial view of a surgical robotic arm, in accordance with an embodiment.

FIG. 2 is a pictorial view of an exemplary surgical robotic manipulator which may include the strain wave gearing with input to output braking, as disclosed herein. Representatively, the robotic manipulator may include a robotic arm 104, a tool drive 220, and a cannula 221 loaded with a robotic surgical tool 250, in accordance with aspects of the subject technology. As shown in FIG. 2, the example surgical robotic arm 104 may include a plurality of links (e.g., links 201-208A-B) and a plurality of actuated joint modules (e.g., joints 211-217) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 220 attached to the distal end of the robotic arm 104. The tool drive 220 may include a cannula 221 coupled to its end to receive and guide a surgical instrument 250 (e.g., endoscopes, staplers, etc.). The surgical instrument (or "tool") 250 may include an end effector having a robotic wrist 252 and jaws 254 at the distal end of the tool. The plurality of the joint modules of the robotic arm 104 can be actuated to position and orient the tool drive 220, which actuates the end effector (e.g., robotic wrist 252 and jaws 254) for robotic surgeries.

In some variations, the plurality of links and joints of the robotic arm 104 can be divided into two segments. The first segment (setup arm) includes links 201-205 and joints 211-215 (also referred to as joints J1-J5) that provide at least five degrees of freedom (DOFs). The proximal end of the first segment can be mounted to a fixture (e.g., surgical table) at the pivot joint 260 (also referred to as joint J0), while the distal end is coupled to the second segment. The second segment (spherical arm) includes links 206-208 providing the arm with at least two DOFs. Link 208 may comprise a first link 208A and a second link 208B operatively coupled with a pulley mechanism to form a parallelogram and to constrain the movement of the tool drive 220 around a mechanical remote center of motion (RCM). The first segment may be referred to as the setup arm because it may position and adjust the RCM in space relative to the mounting fixture, while the second segment may be referred to as the spherical arm because it is configured to move the surgical tool within the generally spherical workspace. In one aspect, the strain wave gearing with input to output braking as disclosed herein may be integrated within the pivot joint 260 (e.g., joint J0) to lock or otherwise brake arm 104 at a desired position once pivoted to/from the storage position under the table and/or operating position over the table. In further aspects, the strain wave gearing may be integrated within any one or more of the other arm joints disclosed herein (e.g., joints 211-215).

Figure 3:
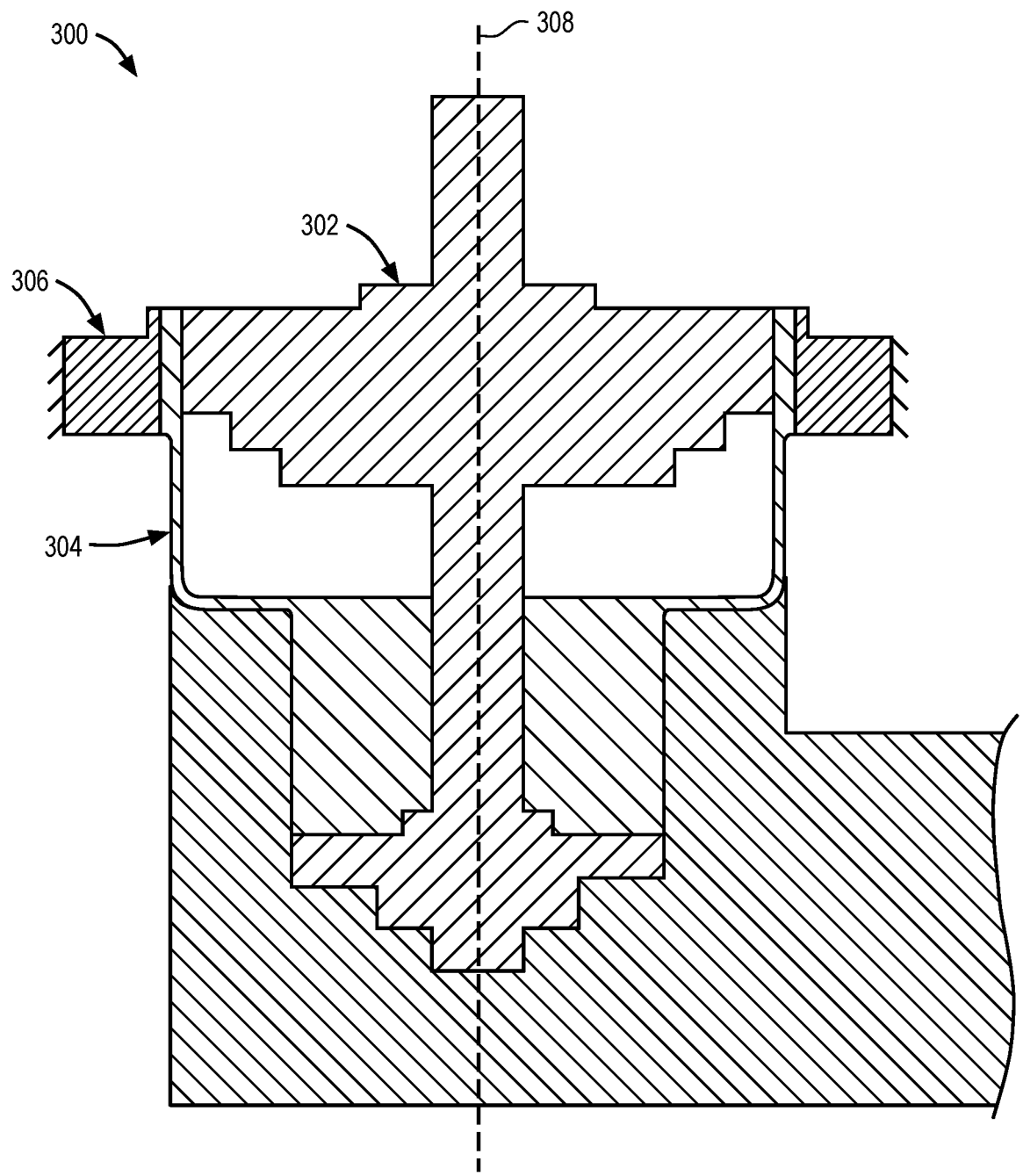
FIG. 3 is a simplified pictorial view of strain wave gearing for use in a surgical robotic arm, in accordance with another embodiment.

FIG. 3 illustrates a simplified schematic diagram of one exemplary strain wave gearing with input to output braking. Representatively, strain wave gearing 300 includes an input portion 302, an output portion 304 and a fixed portion 306, which are all arranged around a common axis 308 (e.g., rotational axis). The input portion 302 may be rigidly attached to a motor drive shaft such that rotation of the motor drive shaft may drive a rotation of the input portion 302 around axis 308. The output portion 304 is arranged concentrically outward to the input portion 302 and may rotate relative to the input portion 302, also around axis 308. The fixed portion 306 may be arranged concentrically outward to the input portion 302 and the output portion 304 and may be fixed to a housing (e.g., the robotic arm housing) within which the strain wave gearing is integrated. Both the input portion 302 and the output portion 304 may rotate relative to the fixed portion 306 to cause a movement of a driven component (e.g., surgical robotic arm). Typically, in gearing systems, as previously discussed, braking of the system is accomplished by braking an input or output shaft to the housing, and therefore requires a relatively large braking mechanism. Braking of strain wave gearing 300, in contrast, is accomplished by mechanically braking (e.g., holding and/or stopping motion) input portion 302 to output portion 304. In other words, during a braking operation, input portion 302 is locked to output portion 304 such that they can no longer move relative to one another, which in turn, prevents a net output movement (e.g., to drive the associated driven component). The input portion 302, output portion 304, fixed portion 306 and/or braking assembly may all be considered to share, be mounted on or otherwise aligned, along axis 308. In some aspects, an axial movement of one or more of the strain wave gearing components and/or braking assembly along the axis 308 may be used to brake the input to the output. The specific components of the strain wave gearing 300 which allow for input to output breaking will now be described in reference to FIG. 4-FIG. 6.

Figure 4:
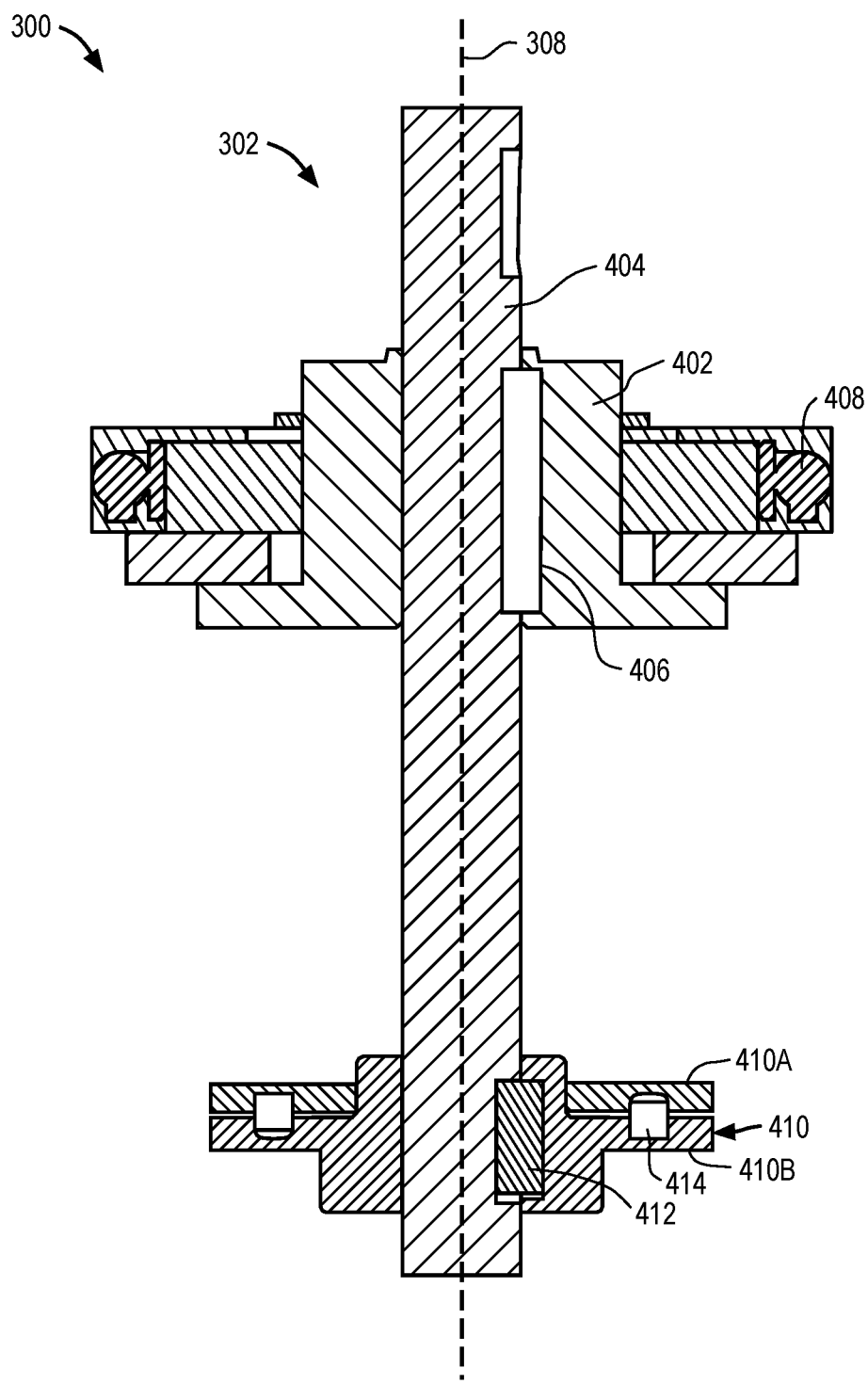
FIG. 4 is a simplified pictorial view of an input portion of the strain wave gearing of FIG. 3.
Figure 5:
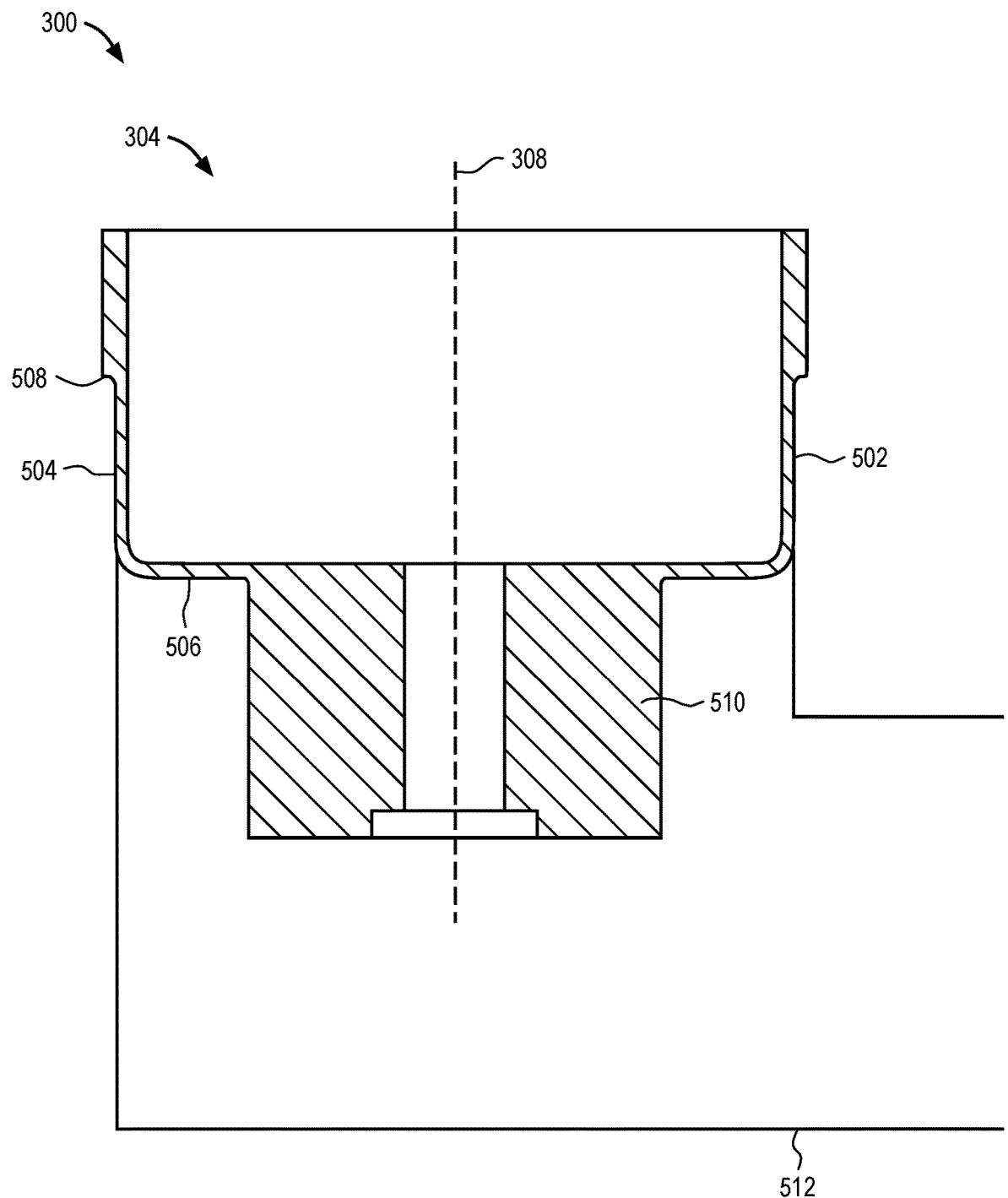
FIG. 5 is a simplified pictorial view of an output portion of the strain wave gearing of FIG. 3.
Figure 6:
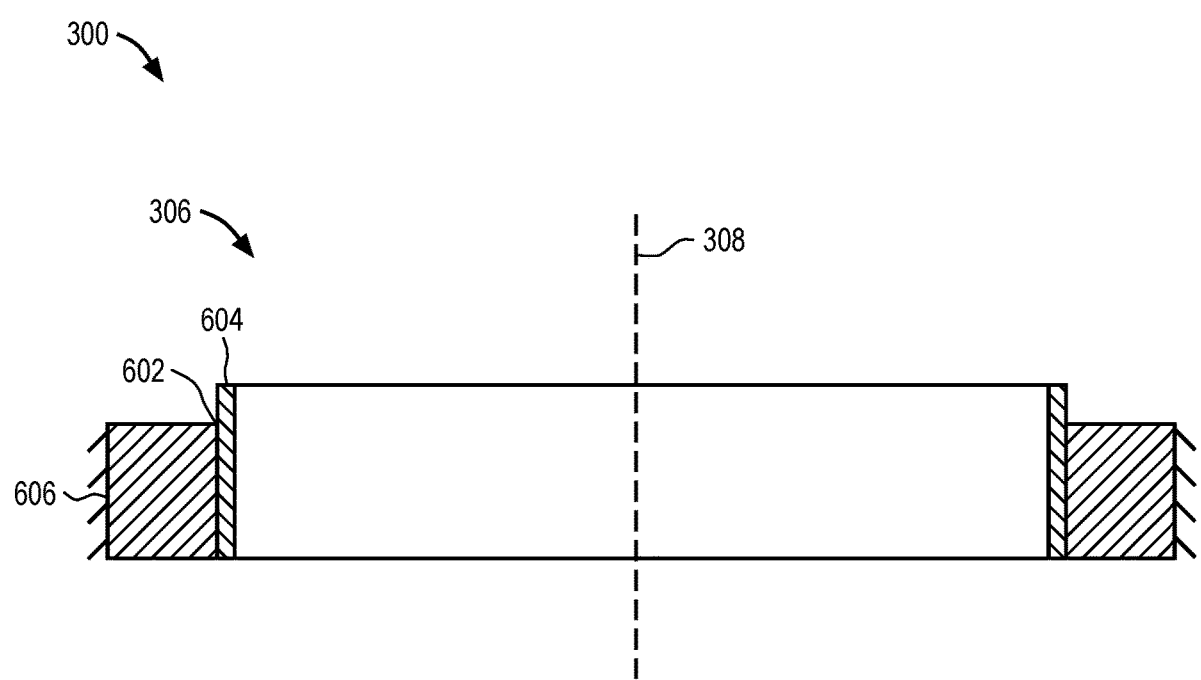
FIG. 6 is a simplified pictorial view of a fixed portion of the strain wave gearing of FIG. 3.

FIG. 4 illustrates a schematic side view of the input portion 302, FIG. 5 illustrates a schematic side view of the output portion 304, and FIG. 6 illustrates a schematic side view of the fixed portion 306, previously discussed in reference to FIG. 3. Referring now to FIG. 4, input portion 302 includes a wave generator 402 attached to an input shaft 404. The wave generator 402 may be, for example, an elliptical disk, also known as an elliptical plug, which is positioned around shaft 404. In one aspect, input shaft 404 may include a shaft key 406 positioned along a portion of the shaft within the wave generator 402, and the shaft key 406 attaches the wave generator 402 to the input shaft 404. Although not shown, the input shaft 404 may be fixedly attached to a motor shaft which drives movement of the input shaft 404, and in turn, the wave generator 402. The wave generator 402 may further include an oldham coupler 408 that movably couples the input portion 302 to output portion 304. Input portion 302 may further include first braking member 410 fixedly attached to the other end of the input shaft 404 by shaft key 412. The first braking member 410 may be a hub which forms the first part of the braking mechanism or assembly used to brake the input portion 302 to the output portion 304. The first braking member 410 may, for example, be a disk shaped member positioned around the end of input shaft 404, and below the output portion 304, as shown. In some aspects, first braking member 410 may include a top portion 410A and a bottom portion 410B, which are movably coupled to one another by a connecting member 414. The top plate 410A and/or the bottom plate 410B may move in an axial direction (e.g., a direction parallel to axis 308) to engage/disengage the first braking member 410 with a second braking member (e.g., second braking member 510 shown in FIG. 5) during a braking operation. For example, the connecting member 414 may be, or include, a spring that allows top plate 410A and/or bottom plate 410B to move in an axial direction relative to one another. Representatively, first braking member 410 may be, or be part of a spring set brake, which includes the top and bottom plates 410A, 410B, a spring (e.g. connecting member 414) biasing the plates away from one another, and an electromagnet coil. The electromagnet coil could be, for example, incorporated into, or otherwise form a part of, or be coupled to, the second braking member 510. During operation, the electromagnet coil can be powered by a DC voltage which creates a magnetic field strong enough to override the biasing force created by the spring and pull the plates 410A, 410B together, in the axial direction. This, in turn, forms a gap between the input portion 302 (including first braking member 410) and the output portion 304 (including the second braking member 510 shown in FIG. 5), and allows them to move relative to one another. To initiate a braking operation (e.g., prevent movement of the output portion 304 relative to the input portion 302), the voltage is removed allowing the spring to once again push the plates 410A, 410B away from one another, causing the top plate 410A of the first braking member 410 to contact the second braking member on the input portion 302, and brake the input portion 302 to the output portion 304.

As illustrated by FIG. 5, the output portion 304 may include a flex spline or flex cup 502, which is positioned around the wave generator 402 (not shown). The flex cup 502 may be shaped like a cup and have a relatively flexible side wall 504 that is open at one end and coupled to a relatively rigid bottom wall 506 at another end. The flex cup 502 may be attached to an output shaft 512, which in turn, is attached to the driven component or is part of the driven component. Flex cup teeth 508 may be radially positioned around the outer surface of the side wall 504, near the open end. As illustrated in FIG. 6, the fixed portion 306 includes a circular spline (e.g., rigid ring) having an inner surface 602 including radially positioned circular spline teeth 604 and the outer surface 606 is fixedly attached to the surrounding housing.

During operation, a rotation of the elliptically shaped wave generator 402 within the flex cup 502 causes the flex cup side wall 504 to deform, and in turn, the flex cup teeth 508 to engage with the circular spline teeth 604 of the circular spline and drive a rotation of the flex cup 502. For example, as the wave generator 402 rotates in a first direction (e.g., clockwise direction), the flex cup side wall 504 deforms causing the flex cup teeth 508 to mesh with the circular spline teeth 604. The flex cup 502 includes fewer teeth than the circular spline such that for every full rotation of the wave generator 402, the flex cup 502 rotates a small amount in a second direction (e.g., a counter clockwise direction), relative to the circular spline. This movement of the flex cup 502, which is part of the output portion 304, in turn, drives a desired movement of the associated driven component (e.g., a surgical robotic arm).

If the movement of the flex cup 502 relative to the wave generator 402, however, is prevented, there is no net output movement. In this aspect, the second braking member 510 is attached to the flex cup 502 so that the second braking member 510 in combination with the first braking member 410 can be used to prevent the relative movement between flex cup 502 and wave generator 402. For example, second braking member 510 may be fixedly attached to, or otherwise near, the bottom wall 506 of flex cup 502, as illustrated by FIG. 5. In one aspect, the second braking member 510 may be a housing which contains, or otherwise includes, the electromagnet coil and a permanent magnet. The first braking member 410 and the second braking member 510 may be axially aligned (e.g., along axis 308), or otherwise arranged such that one is above/below the other. Braking may occur when first braking member 410 and/or second braking member 510 are moved in an axial direction (e.g., in a direction parallel to the axis 308) toward one another to prevent the relative movement between wave generator 402 and flex cup 502 (e.g., brake the input portion 302 to the output portion 304), or away from one another (e.g., to release the braking assembly). In some cases, the braking assembly or mechanism may be a spring or spring set brake which includes a spring to help driving the braking action. In other aspects, the braking assembly or mechanism may be a permanent magnet brake. In the case of a permanent magnet brake, the first braking member 410 may include a metallic surface (e.g., top component 410A) that faces the permanent magnet (e.g., second braking member 510) and a magnetic force is used to engage the braking components and brake the input to the output.

Figure 7:
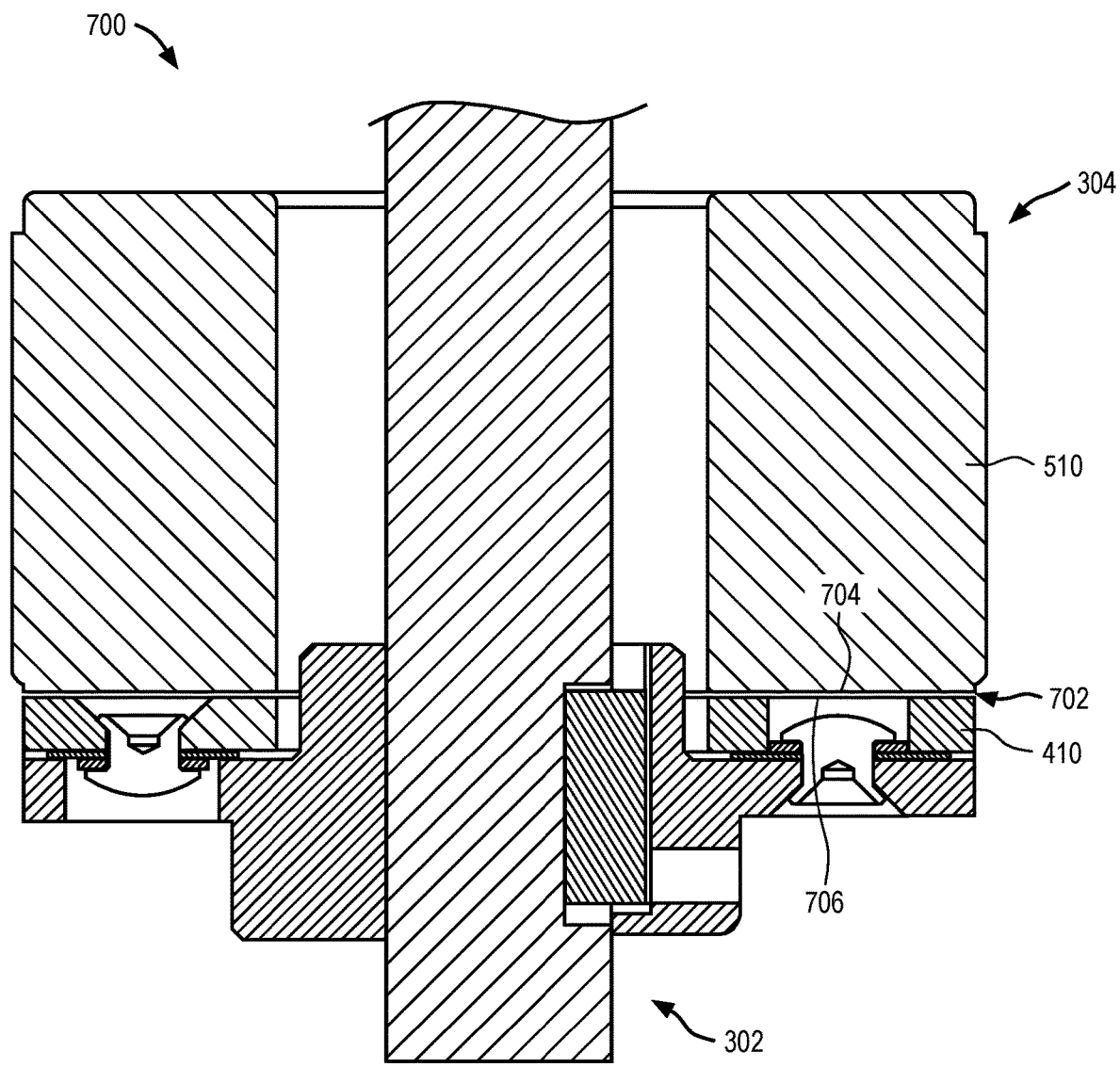
FIG. 7 is a magnified view of a disengaged braking assembly of the strain wave gearing of FIG. 3.
Figure 8:
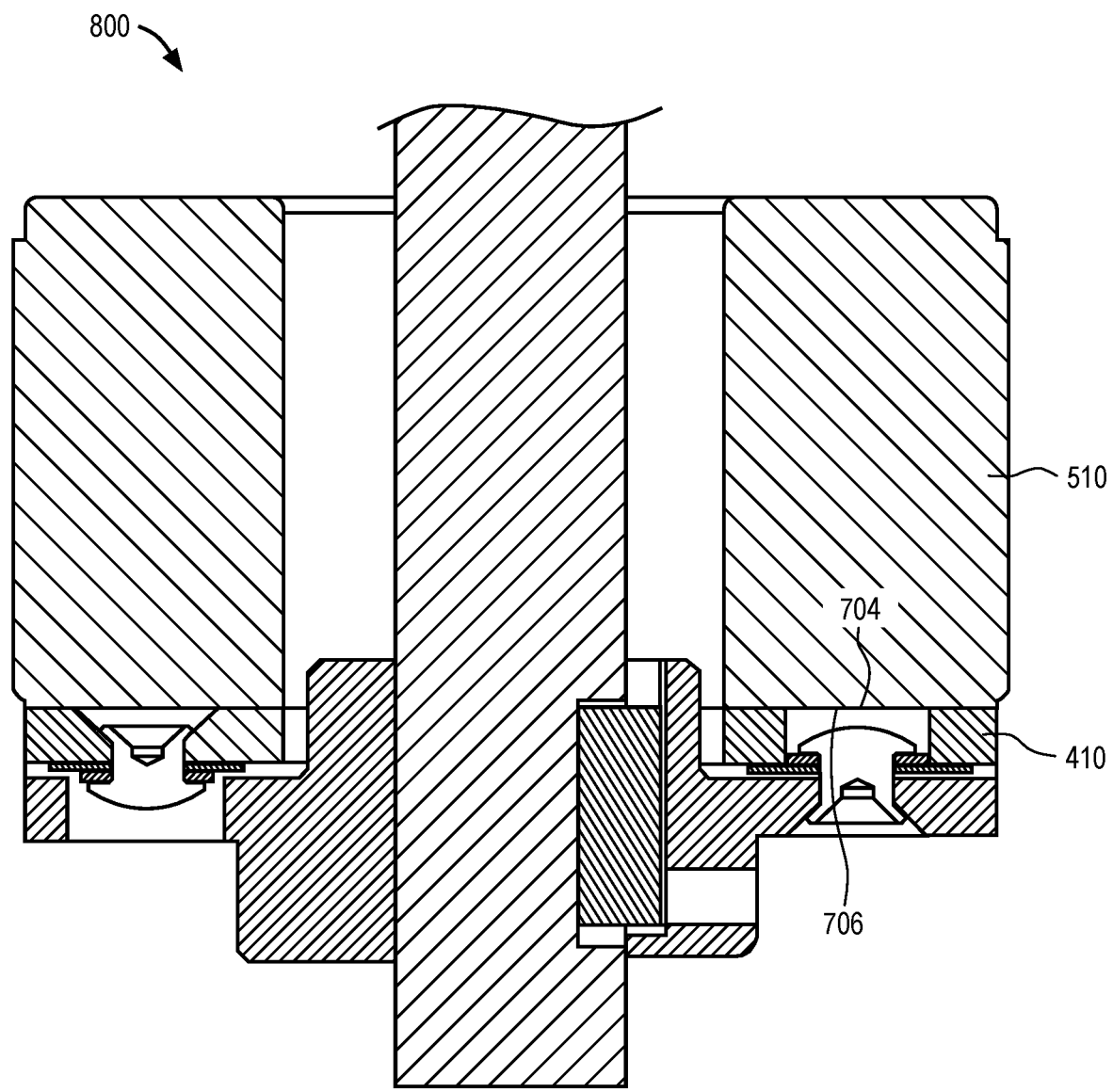
FIG. 8 is a magnified view of an engaged braking assembly of the strain wave gearing of FIG. 3.

Representatively, FIG. 7 and FIG. 8 illustrate magnified views of the braking assembly in both the disengaged and engaged positions. In particular, as can be seen from FIG. 7, when the braking assembly is in the disengaged position 700, a space or gap 702 is present a top side 706 of the first braking member 410 and a bottom side 704 of second braking member 510. This gap 702 allows the input portion 302 (e.g., wave generator 402) to move (e.g., rotate) relative to the output portion 304 (e.g., flex cup 502), and in turn there is a net output movement to a driven member associated with output portion 304. In the engaged position 800 shown in FIG. 8, the first braking member 410 and the second braking member 510 are pressed together such that the gap is closed and their interfacing sides 704, 706 are in contact with one another as shown. For example, first braking member 410 may include a spring as previously discussed which drives the movement of first braking member 410 axially according to the arrow (e.g., parallel to the axis of rotation) to transition the braking assembly between the disengaged and engaged positions. In the engaged position 800, the relative movement (e.g., rotation) between input portion 302 (e.g., wave generator 402) and output portion 304 (e.g., flex cup 502) is prevented. This, in turn, prevents a net output movement and brakes the input to the output so that no further movement can occur. In some aspects, the engaged position 800 occurs in the absence of power, and power must be applied to transition the assembly to the disengaged position 700. For example, in one aspect, a spring may bias at least one of the braking members away from the other braking member in the absence of power. When power is applied, an electromagnetic force is generated that overrides the biasing force of the spring and causes the at least one braking member to move toward the other braking member to the engaged position 800. In other embodiments, the permanent magnet may be omitted and an entirely spring controlled braking assembly may be used. In some aspects, the frictional force between the braking members is used to prevent movement of the braking members relative to one another during the braking operation. It is further contemplated that in other embodiments, a magnetic force is generated which prevents movement of the braking members relative to one another. Regardless of the braking force used, it should be appreciated that because the braking assembly is integrated into the strain wave gearing, and in turn brakes the input to the output, as opposed to braking, for example, the output to the housing, the braking assembly can be relatively small while still achieving a maximum braking function.

It should be understood that although input portion 302 is described herein as a wave generator 402 and output portion 304 is described as a flex spline or flex cup 502, the specific strain wave gearing components making up the input and output portions may be interchanged or reversed. For example, input portion 302 may be a wave generator, a flex spline or circular spline, and output portion 304 may be the other of a flex spline (or flex cup), a wave generator or a circular spline. In addition, in some aspects, the fixed portion 306 may be a circular spline or wave generator. Representatively, contemplated alternative arrangements may include (1) the input portion may be a wave generator, the output portion may be a flex spline (or flex cup) and the fixed portion may be a circular spline; (2) the input portion may be a wave generator, the output portion may be a circular spline and the fixed portion may be a flex spline (or flex cup); (3) the input portion may be a flex spline, the output portion may be a circular spline and the fixed portion may be a wave generator; (4) the input portion may be a circular spline, the output portion may be a flex spline (or flex cup) and the fixed portion may be a wave generator; (5) the input portion may be a flex spline (or flex cup), the output portion may be a wave generator, and the fixed portion may be a circular spline; and/or (6) the input portion may be a circular spline, the output portion may be a wave generator and the fixed portion may be flex spline (or flex cup). It is contemplated that in some aspects when all of the wave generator, the flex spline and the circular spline rotate, combinations (1)-(6) are possible.

Figure 9:
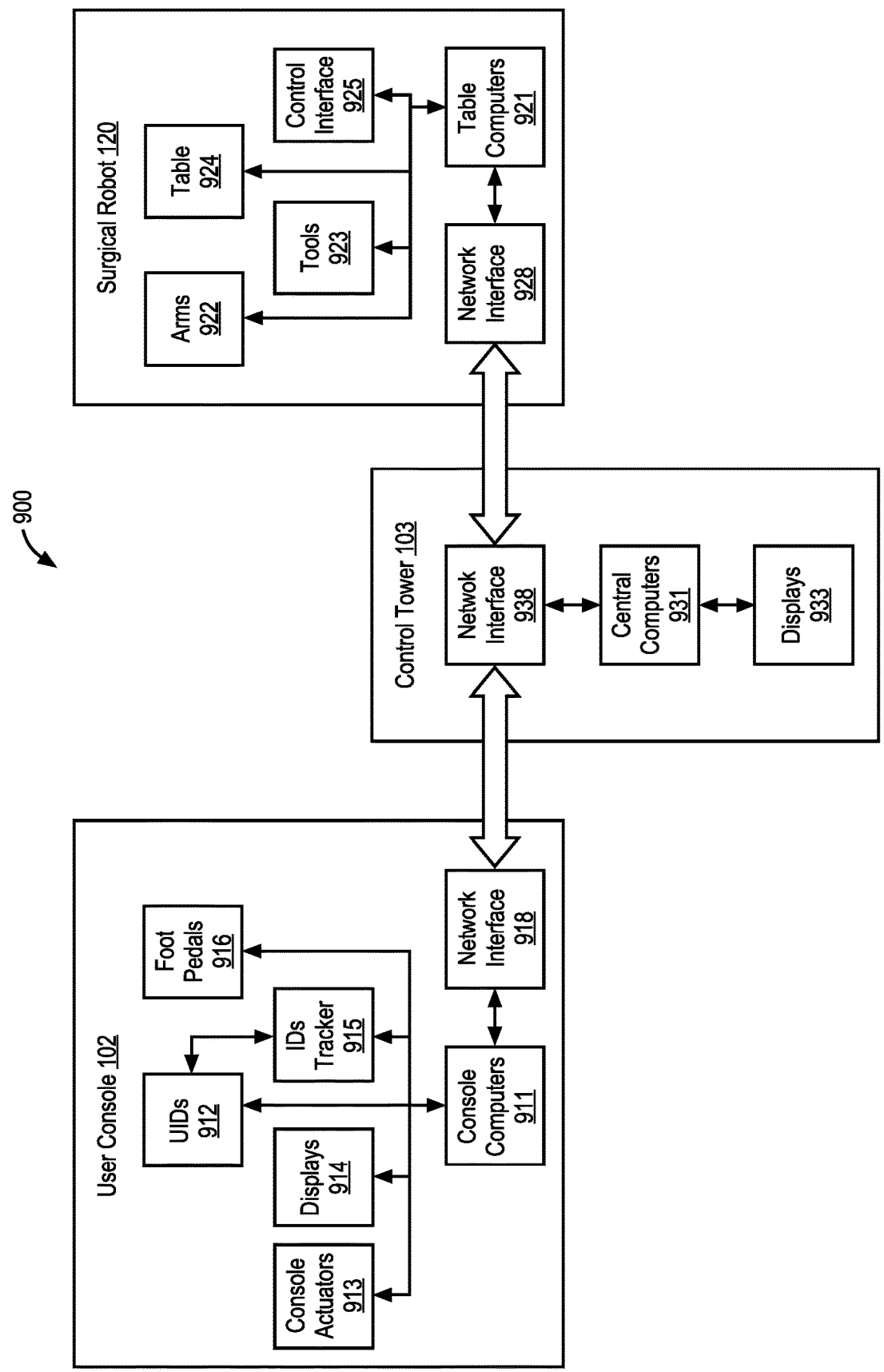
FIG. 9 is a block diagram of a computer portion of a surgical robotic system, in accordance with an embodiment.

Referring now to FIG. 9, FIG. 9 is a block diagram of a computer portion of a surgical robotic system, in accordance with an embodiment. The exemplary surgical robotic system 900 may include a user console 102, a control tower 103, and a surgical robot 120. The surgical robotic system 900 may include other or additional hardware components; thus, the diagram is provided by way of example and not a limitation to the system architecture.

The user console 102 may include console computers 911, one or more UIDs 912, console actuators 913, displays 914, a UID tracker 915, foot pedals 916, and a network interface 918. A user or surgeon sitting at the user console 102 can adjust ergonomic settings of the user console 102 manually, or the settings can be automatically adjusted according to user profile or preference. The manual and automatic adjustments may be achieved through driving the console actuators 913 based on user input or stored configurations by the console computers 911. The user may perform robot-assisted surgeries by controlling the surgical robot 120 using one or more master UIDs 912 and foot pedals 916. Positions and orientations of the UIDs 912 are continuously tracked by the UID tracker 915, and status changes are recorded by the console computers 911 as user input and dispatched to the control tower 103 via the network interface 918. Real-time surgical video of patient anatomy, instrumentation, and relevant software apps can be presented to the user on the high resolution 3D displays 914 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electromagnetic or optical trackers are included at the user console 102 for improved ergonomics.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 9, the control tower 103 may include central computers 931 including at least a visualization computer, a control computer, and an auxiliary computer, various displays 933 including a team display and a nurse display, and a network interface 938 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 may include an articulated operating table 924 with a plurality of integrated arms 922 that can be positioned over the target patient anatomy. A suite of compatible tools 923 can be attached to or detached from the distal ends of the arms 922, enabling the surgeon to perform various surgical procedures. The surgical robot 120 may also comprise control interface 925 for manual control of the arms 922, table 924, and tools 923. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 922 includes four arms mounted on both sides of the operating table 924, with two arms on each side. For certain surgical procedures, an arm mounted on one side of the table can be positioned on the other side of the table by stretching out and crossing over under the table and arms mounted on the other side, resulting in a total of three arms positioned on the same side of the table 924. The surgical tool can also comprise table computers 921 and a network interface 928, which can place the surgical robot 120 in communication with the control tower 103.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

The invention claimed is:

1. A surgical robotic system comprising a braking assembly comprising:
   a first braking member having a first portion and a second portion operable to move relative to the first portion; and
   a second braking member that is engaged by the second portion during a braking operation to mechanically brake an input portion to an output portion of a strain wave gear coupled to a surgical robotic manipulator, and the second braking member comprises an electromagnet.

2. The surgical robotic system of claim 1 wherein the first braking member and the second braking member are axially aligned, and during the braking operation, the second portion of the first braking member moves in an axial direction and contacts the second braking member to prevent rotation of the input portion relative to the output portion.

3. The surgical robotic system of claim 1 wherein the braking assembly comprises a spring set brake or a permanent magnet brake.

4. The surgical robotic system of claim 1 wherein the second portion of the first braking member comprises a disk that is movable in an axial direction relative to the second braking member and the braking operation occurs in an absence of power.

5. The surgical robotic system of claim 1 wherein the input portion comprises an input shaft fixedly coupled to a wave generator that is rotatably coupled to the output portion, the second portion comprises a disk coupled to the input shaft, the output portion comprises a flex cup that is rotatably coupled to the input portion, the second braking member is coupled to the flex cup, and a fixed portion is positioned concentrically outward to the input portion and the output portion.

6. The surgical robotic system of claim 1 wherein the surgical robotic manipulator comprises a surgical robotic arm having a number of links connected by a number of joints, and one of the joints comprises the strain wave gear.

7. A surgical robotic system comprising a braking assembly comprising:
   an input portion comprising a wave generator fixedly coupled to an input shaft;
   an output portion comprising a flex cup fixedly coupled to an output shaft, and the input portion rotates to drive a relative movement between the input portion and the output portion;
   a fixed portion comprising a circular spline that engages with the flex cup to rotate the output portion relative to the fixed portion; and
   a braking assembly operable to prevent a relative movement between the input portion and the output portion during a braking operation.

8. The surgical robotic system of claim 7 wherein the braking assembly comprises a first braking member and a second braking member, and wherein a movement of the first braking member or the second braking member in an axial direction transitions the braking assembly between an engaged position in which the first braking member engages the second braking member to prevent movement between the input portion and the output portion and a disengaged position in which there is a gap between the first braking member and the second braking member.

9. The surgical robotic system of claim 8 wherein the first braking member is coupled to the input portion and operable to rotate with the input shaft and move in an axial direction, and the second braking member is coupled to the output portion.

10. The surgical robotic system of claim 9 wherein the first braking member comprises a top component and a bottom component, wherein the top component or the bottom component is operable to move in the axial direction relative to the other.

11. The surgical robotic system of claim 8 wherein the second braking member comprises an electromagnet coil and a permanent magnet fixedly coupled to the output portion.

12. The surgical robotic system of claim 7 wherein the input portion, the output portion, the fixed portion and the braking assembly are aligned along a common axis.

13. The surgical robotic system of claim 7 wherein the surgical robotic system comprises a surgical robotic arm having a number of links connected by a number of joints, and one of the joints connecting the surgical robotic arm to a fixed structure comprises the braking assembly.

14. A surgical robotic system comprising a braking assembly comprising:
   a first surgical robotic component;
   a second surgical robotic component coupled to the first surgical robotic component, the second surgical robotic component operable to move relative to the first surgical robotic component and comprising a strain wave gear; and
   a braking assembly operable to brake a movement of the second surgical robotic component relative to the first surgical robotic component by preventing a relative movement between a wave generator and a flex cup of the strain wave gear during a braking operation, the braking assembly having a first braking member comprising a first plate and a second plate movable in an axial direction relative to the first plate, and a second braking member that is engaged by the second plate during a braking operation.

15. The surgical robotic system of claim 14 wherein the second surgical robotic component comprises a surgical robotic arm comprising a plurality of links and a plurality of joints, at least one joint of the plurality of joints is a pivot joint connecting the surgical robotic arm to the first surgical robotic component, and the strain wave gear is coupled to the pivot joint.

16. The surgical robotic system of claim 14 wherein at least one of the first braking member or the second braking member is attached to the flex cup, and wherein the first braking member and the second braking member directly engage with one another during the braking operation.

17. The surgical robotic system of claim 16 wherein during a non-braking operation, the first braking member and the second braking member are operable to rotate relative to one another around a common axis.

18. The surgical robotic system of claim 14 wherein the first braking plate or the second plate comprises a metal disk-plate and the second braking member comprises a permanent magnet.

19. The surgical robotic system of claim 14 wherein the braking assembly comprises a spring set brake.

20. The surgical robotic system of claim 14 wherein the strain wave gear further comprises a circular spline, and the wave generator, the flex cup, the circular spline and the braking assembly are aligned along a common axis.

* * * * *

UNITED STATES PATENT AND TRADEMARK OFFICE
CERTIFICATE OF CORRECTION

| | | |
|---|---|---|
| PATENT NO. | : 12,318,163 B2 | Page 1 of 1 |
| APPLICATION NO. | : 18/316665 | |
| DATED | : June 3, 2025 | |
| INVENTOR(S) | : Bharat Thakkar | |

It is certified that error appears in the above-identified patent and that said Letters Patent is hereby corrected as shown below:

In the Claims

Column 15
Line 20, Claim 18, delete "braking" before "plate"
Line 20, Claim 18, delete "disk-" before "plate"

Signed and Sealed this
Twenty-ninth Day of July, 2025

Coke Morgan Stewart
*Acting Director of the United States Patent and Trademark Office*